United States Patent
Kim et al.

(10) Patent No.: US 6,663,884 B2
(45) Date of Patent: Dec. 16, 2003

(54) METHOD OF DETOXIFYING THE EGG OF PUFFER FISH FOR CREATING HEALTHY FOODSTUFFS AND THE RESULTING PRODUCT

(76) Inventors: Sang Kuen Kim, 319-10, Hapcheon-ri, Hapcheon-eup, Hapcheon-gun, Gyeongsangnam-do (KR); Byoung Ki Kim, 319-10, Hapcheon-ri, Hapcheon-eup, Hapcheon-gun, Gyeongsangnam-do (KR); Jung Sik Shin, 101-602, Hwang Je Mansion, 11-8, Naedang-Dong, Seo-Gu, Daegu (KR); Jin San Shin, 101-602, Hwang Je Mansion, 11-8, Naedang-Dong, Seo-Gu, Daegu (KR)

( * ) Notice: Subject to any disclaimer, the term of this patent is extended or adjusted under 35 U.S.C. 154(b) by 0 days.

(21) Appl. No.: 10/212,115

(22) Filed: Aug. 6, 2002

(65) Prior Publication Data

US 2003/0211226 A1 Nov. 13, 2003

(30) Foreign Application Priority Data

May 7, 2002 (KR) ........................................ 2002-25102

(51) Int. Cl.$^7$ .......................... A61K 47/00; A61K 9/00; A61K 9/14; A61K 9/20; A61K 9/48
(52) U.S. Cl. ....................... 424/439; 424/400; 424/451; 424/464; 424/489
(58) Field of Search ................................. 424/439, 400, 424/451, 464, 489

(56) References Cited

U.S. PATENT DOCUMENTS 6,171,626 B1 * 1/2001 Lagos et al. ................. 426/324

* cited by examiner

*Primary Examiner*—Thurman K. Page
*Assistant Examiner*—Simon J. Oh
(74) *Attorney, Agent, or Firm*—Birch, Stewart, Kolasch & Birch, LLP

(57) ABSTRACT

A method of detoxifying the egg of puffer fish for creating healthy foodstuffs which includes the steps of heating the eggs of puffer fish and ginger root at a temperature of 100–200° C. for 30–40 minutes and drying the heated egg composition, and repeating the heating and drying steps a multiplicity of times to produce a detoxified product.

9 Claims, No Drawings

METHOD OF DETOXIFYING THE EGG OF PUFFER FISH FOR CREATING HEALTHY FOODSTUFFS AND THE RESULTING PRODUCT

BACKGROUND OF THE INVENTION

1. Field of the Invention

The present invention relates to an improved method of detoxifying the egg of puffer fish for creating a healthy foodstuff and more particularly, to a method for manufacturing a medicinal foodstuff utilizing the egg of puffer fish, which is has been detoxified and which can be used in treating patients who suffer from various types of illness and tumors, such as hepatitis, liver tumor, liver cirrhosis, liver cancer, stomach cancer, lung cancer, colon cancer, and bronchial cancer, and lung disease, bronchitis, hangover and fatigue. The present invention is also directed to the detoxified egg composition manufactured by the present method.

2. Description of Related Art

There are many types of known healthy foodstuffs such as extracts, teas and juices obtained from natural substances such as herbs, fishes and animals.

Cancer is a malignant tumor of potentially unlimited growth that expands locally by invasion and systemically by metastasis. Cirrhosis of the liver is a fibrosis of the liver wherein hardening of the organ is caused by the excessive formation of connective tissue followed by contraction. According to statistics, one-fifth of the patients diagnosed with cirrhosis of the liver develop liver cancer.

Gastrointestinal cancer has the highest frequency of occurrence in both sexes and colon and rectum involvement is the most prevalent. Carcinoma of the stomach is also a frequently occurring disease. Treatment of gastrointestinal cancer essentially is generally confined to surgery, radiation, chemotherapy, or combinations thereof.

The lung cancer has been statistically linked to tobacco smoking and continues to present a poor prognosis, thus giving emphasis to limiting exposure of the lungs to carcinogenic materials. The primary types of lung cancer are bronchogenic carcinoma, and bronchiolar or alveolar carcinoma. Greater success has been obtained with multiple drug therapy which has produced good results in a number of patients with the non-oat cell type of cancers. Drugs found to have some success include cyclophosphanmide, methotrexate, and vincristine.

Liver cancer is a malignant collection of abnormal and uncontrollably growing cells that are derived from hepatocytes, the epithelial cells of the liver, and is called hepatocellular carcinoma. Risk factors in the development of liver cancer include chronic infection with the hepatitis B virus and cirrhosis. Treatment of liver cancers is generally confined to drug therapy or radiation therapy.

Conventional foodstuffs used in medical treatment suffer from a number of problems. For example, when such conventional chemical foodstuffs such as conventional herbs, are given to the humans, harmful side effects are frequently experienced. Even though the meat of the puffer fish is considered a kind of healthy foodstuff, the egg of puffer fish cannot be eaten since it has a toxic character.

SUMMARY OF INVENTION

Accordingly, it is an object of the present invention to provide a method of detoxifying the egg of puffer fish for creating a healthy foodstuff which eliminates the above problems encountered with conventional methods of detoxifying the egg of puffer fish.

Another object of the present invention is to provide a detoxified egg composition of the puffer fish for creating a healthy foodstuff, which can be used to treat various types of diseases such as cancers, hepatitis, bronchitis, lung disease, hangover, fatigue and the like. Thus, the detoxified egg composition exhibits anticancer and anti-inflammation properties.

A further objection of the present invention is to provide an improved method of detoxifying the egg of puffer fish for creating healthy foodstuffs which comprises the steps of treating the puffer fish eggs with ginger root in an amount of about 1:2 by weight in a container, by heating the composition at a temperature of about 100–200° C. for about 30–40 minutes to produce a cooked product, drying the cooked product for about 20–30 hours at room temperature or preferably under the sun, repeating the heating and drying steps about 6–7 times to produce a cooked and dried product, and sterilizing the cooked and dried product thus producing a healthy foodstuff.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Referring now in detail to the purpose of illustrating preferred embodiments of the present invention, there is provided a method of detoxifying the egg of puffer fish for creating healthy foodstuffs. The method according to the present invention comprises the steps of (a) gathering the egg from the puffer fish, (b) cleaning the gathered egg of the step (a), (c) heating the egg and ginger root in an amount of about 1200 g and 600 g, respectively in a container at a temperature of about 100–200° C. for about 30–40 minutes to produce cooked egg, (d) drying the cooked egg the step (c) at room temperature for about 20–30 hours or under the sun, (e) repeating the heating step (c) and the drying step (d) about 6–7 times to produce a final product, (f) sterilizing the final product in a steam container for about 30–60 minutes or under the sun for about 10–20 hours, (g) and preparing a capsular preparation or a granular preparation of pulverized egg.

In the heating step (c) and the repeating step (e), it is better to cover the bottom of the heating container with the ginger root. The species of the ginger root natural substance, according to the present invention is Zingiber officinale Roscoe. Also, in the steps (c) and (g), the raw egg of puffer fish and ginger root are present in a preferred amount of about 1:2 by weight, respectively. In the pulverizing step (h), a preferred powder size of the produced powder is the same as the size of conventional wheat flour.

The puffer fish, according to the present invention, is common species of Spheroids Maculates native to the Atlantic Coast of the United States and can distend its body to a globular form and float belly upward on the surface of the water. The puffer fish has the toxin tetrodotoxin ($C_{12}H_{19}N_3O_9$) which is also called puffer toxin or spheroidine. The tetrodotoxin has an atomic mass unit of 350, is a white column crystal with a decomposition point of 240° C., and is soluble in water. Also, this toxin is found in the ovary and the liver, with little or no presence in the skin, intestines, blood and eggs, and is nonexistent in the meat and spermary of the puffer fish. Tetrodotoxin can be used as a medicine for treating neuralgia, arthralgia, and rheumatism.

Accordingly, in order to use the egg of the puffer fish, the toxin from the egg thereof must be removed. The present invention removes the toxin from the egg of the puffer fish by following the above-identified method. The present invention reduces the toxin to a residual amount of tetrodotoxin by heating the egg of puffer fish and raw ginger root at a temperature of about 100–200° C. for about 30–40 minutes, and repeating the drying step 6–7 times. Thus, the final product containing a residual amount can be utilized as a healthy foodstuff.

The present invention will now be described in more detail in connection with the following steps:

(a) Gathering

Raw eggs of puffer fish are gathered from raw puffer fish in order to manufacture a good quality of the detoxified egg of puffer fish for use in healthy foodstuffs.

(b) Cleaning

The raw eggs of puffer fish from step (a) must be cleaned carefully in clear water such as flowing river, causing a frequent breaking of the egg sac in the cleaning step. For example, the raw eggs are placed in a net container and cleaned with flowing river water.

(c) Heating

Cleaned ginger root is cut into slices and 1200 g of these slices are used to cover the bottom of the heating container. Thereafter, 600 g of the cleaned fish eggs are added to cover the ginger root floor. The container of 1200 g of ginger root and 600 g of puffer fish eggs is heated by a conventional heat source at a temperature of about 100–200° C. for 30–40 minutes to produce a cooked egg composition. Over 40 minutes, the ginger root burns and less than 30 minutes, the ingredients of the ginger root are not completely extracted. Thus, 30–40 minutes has been found to be a preferable heating time, at a preferred temperature of 150° C.

(d) Drying

The cooked egg composition separated from the heating container can be dried at room temperature, preferably under sun until the cooked egg composition becomes to be solid, usually requiring about 20–30 hours, preferably 24 hours.

(e) Repeating

The heating step (c) and drying step (d) are repeated about 6–7 times. That is, in a second time, the dried eggs of the drying step (d) cover 1200 g of new ginger root slice floor covered on the bottom of the heating container and are heated by a conventional heat source at a temperature of about 100–200° C. for about 30–40 minutes. Thereafter, the heated eggs are dried under the sun for 20–30 hours. The above step is repeated up to 6–7 times.

(f) Sterilizing

The final egg composition produced from the repeating step (e) is sterilized by steaming in a conventional steaming container for about 30–60 minutes. An earthenware steamer can be preferably used as the steaming container. Subsequently, the steamed eggs are dried under the sun for about 10–20 hours.

(g) Pulverizing

Preparing a capsular preparation which contains 0.5 g of the pulverized egg is achieved by pulverizing the eggs to make a powder, using a conventional grinding device. At this time, the egg composition powder has the same particle size as wheat flour. Accordingly, one capsule, one tablet, one powder pack, or one granule pack which contains 0.5 g of puffer fish egg composition powder, may be administered once a day, or in some cases, two preparation units which total 1 g of puffer fish egg composition powder, may be administered once a day as a healthy foodstuff.

Ginger root of Zingiber officinale Roscoe has ingredients of zingrome, shagaol etc. Even though residual toxin remains in the treated egg composition, the amount is insignificant in the creation of a healthy foodstuff. Therefore, the detoxified egg of the puffer fish according to the present invention can be used in the treatment of various types of cancers, tumors, inflammation, and other diseases.

The present invention will now be described in more detail in connection with the following examples which should be considered as being exemplary and not limiting the present invention:

Test Example 1

Treatment of Hangover

To test the present invention as a hangover remedy, six (6) healthy persons ranging in age from 30 to 50 years (3 persons, 50 years old, 1 person 40 years old, and 2 persons, 30 years old) took 1 capsule containing 0.5 g of detoxified puffer fish egg. The six people drank alcohol heavily but did not experience the normal hangover symptoms of vomiting, fatigue, etc.

Test Example 2

Treatment of Bronchitis

Six (6) patients, all 50 years in age, have contracted bronchitis. All patients began taking 1 capsule containing 0.5 g of detoxified puffer fish egg per day. After 1 month of taking this health foodstuff, 3 persons achieved a 60% recovery from the bronchitis. After 2 months, 3 persons achieved an 80% recovery and 3 persons achieved a 60% recovery of the bronchitis. After 3 months, 3 persons were completely cured.

Test Example 3

Treatment of Cancer

Six (6) patients between the ages of 50 to 60 years old wee identified as containing cancer as follows:

($1^{st}$ term: 2 stomach cancer patients, and $2^{nd}$ term: 2 stomach cancer patients and 2 colon cancer patients). The patients began taking 1 capsule per day containing 0.5 g of detoxified puffer fish egg. After 1 month, no change was noted. However, after 2 months, in the $1^{st}$ and $2^{nd}$ terms of the stomach cancer patients, the cancer cells were noted as not having metastasized. Thus, the cancer cells became inactive.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of detoxifying the eggs of puffer fish for creating a healthy foodstuff which comprises:

(a) providing eggs cleaned and separated from the raw egg sac of puffer fish;

(b) heating said eggs together with ginger root in an amount of 1:2 by weight, respectively, at a temperature of about 100–200° C. for about 30–40 minutes to produce a cooked egg composition;

(c) drying the cooked egg composition at a room temperature for about 20–30 hours;

(d) repeating the heating step (b) and the drying step (c) a multiplicity of times, wherein said heating step (b) includes the cooked egg composition covered on new ginger root slices to produce the final egg composition;

(e) sterilizing the final egg composition for about 30–60 minutes and drying the composition under sun for about 10–20 hours; and (f) pulverizing the sterilized egg composition to prepare a dispensable form of the product.

2. The method of claim 1, wherein said step (a) includes cleaning the raw egg sacs in flowing water.

3. The method of claim 1, wherein step (b) includes heating at a temperature of 150° C. for 30 minutes.

4. The method of claim 1, wherein the step (c) includes drying under the sun for about 20–30 hours to produce a solid product.

5. The method of claim 4, wherein the step (c) includes drying under the sun for 24 hours.

6. The method of claim 1, wherein the sterilizing in step (e) is an earthenware steamer.

7. The method of claim 1, wherein the dispensable form is a capsule, a powder pack, a granule pack, or a tablet.

8. A detoxified egg composition comprising a pharmaceutically acceptable amount of eggs of puffer fish and ginger root.

9. The detoxified egg composition of claim 8, wherein said ginger root is Zingiber officinale Roscoe.

* * * * *